US011805805B2

(12) United States Patent
Ford et al.

(10) Patent No.: US 11,805,805 B2
(45) Date of Patent: Nov. 7, 2023

(54) PURIFICATION OF TOBACCO-DERIVED PROTEIN COMPOSITIONS

(71) Applicant: R.J. Reynolds Tobacco Company, Winston-Salem, NC (US)

(72) Inventors: Kyle Ford, Germanton, NC (US); John-Paul Mua, Advance, NC (US); Nicholas Partain, Owensboro, KY (US); Joshua D. Morton, Evansville, IN (US); Barry Bratcher, Owensboro, KY (US)

(73) Assignee: R.J. Reynolds Tobacco Company, Winston-Salem, NC (US)

( * ) Notice: Subject to any disclaimer, the term of this patent is extended or adjusted under 35 U.S.C. 154(b) by 538 days.

(21) Appl. No.: 16/940,698

(22) Filed: Jul. 28, 2020

(65) Prior Publication Data

US 2020/0352213 A1    Nov. 12, 2020

Related U.S. Application Data

(62) Division of application No. 15/654,834, filed on Jul. 20, 2017, now Pat. No. 10,757,964.

(51) Int. Cl.
| | |
|---|---|
| *A61K 36/81* | (2006.01) |
| *A24B 15/24* | (2006.01) |
| *A23J 3/14* | (2006.01) |
| *A23J 1/00* | (2006.01) |
| *A24B 15/28* | (2006.01) |
| *A24B 15/30* | (2006.01) |
| *C07K 1/14* | (2006.01) |
| *C07K 14/415* | (2006.01) |

(52) U.S. Cl.
CPC ............. *A24B 15/241* (2013.01); *A23J 1/007* (2013.01); *A23J 3/14* (2013.01); *A24B 15/28* (2013.01); *A24B 15/303* (2013.01); *C07K 1/145* (2013.01); *C07K 14/415* (2013.01); *C12Y 401/01039* (2013.01)

(58) Field of Classification Search
CPC ...... A24B 15/24; A24B 15/241; A24B 15/243
See application file for complete search history.

(56) References Cited

U.S. PATENT DOCUMENTS

| | | |
|---|---|---|
| 3,612,065 A | 10/1971 | Rosen |
| 3,684,520 A | 8/1972 | Bickoff et al. |
| 3,823,128 A | 7/1974 | Bickoff et al. |
| 3,943,945 A | 3/1976 | Rosen |
| 3,959,246 A | 5/1976 | Bickoff et al. |
| 4,144,895 A | 3/1979 | Fiore |
| 4,150,677 A | 4/1979 | Osborne, Jr. et al. |
| 4,267,847 A | 5/1981 | Reid |
| 4,268,632 A | 5/1981 | Wildman et al. |
| 4,289,147 A | 9/1981 | Wildman et al. |
| 4,333,871 A | 6/1982 | De Jong |
| 4,340,676 A | 7/1982 | Bourque |
| 4,347,324 A | 8/1982 | Wildman et al. |
| 4,351,346 A | 9/1982 | Brummer et al. |
| 4,359,059 A | 11/1982 | Brummer et al. |
| 4,366,823 A | 1/1983 | Rainer et al. |
| 4,366,824 A | 1/1983 | Rainer et al. |
| 4,388,933 A | 6/1983 | Rainer et al. |
| 4,400,471 A | 8/1983 | Johal |
| 4,506,682 A | 3/1985 | Muller |
| 4,588,691 A | 5/1986 | Johal |
| 4,589,428 A | 5/1986 | Keritsis |
| 4,605,016 A | 8/1986 | Soga et al. |
| 4,641,667 A | 2/1987 | Schmekel et al. |
| 4,716,120 A | 12/1987 | Tsay et al. |
| 4,716,911 A | 1/1988 | Poulose et al. |
| 4,727,889 A | 3/1988 | Niven, Jr. et al. |
| 4,887,618 A | 12/1989 | Bernasek et al. |
| 4,941,484 A | 7/1990 | Clapp et al. |
| 4,967,771 A | 11/1990 | Fagg et al. |
| 4,986,286 A | 1/1991 | Roberts et al. |
| 5,005,593 A | 4/1991 | Fagg |
| 5,018,540 A | 5/1991 | Grubbs et al. |
| 5,060,669 A | 10/1991 | White et al. |
| 5,065,775 A | 11/1991 | Fagg |
| 5,074,319 A | 12/1991 | White et al. |
| 5,099,862 A | 3/1992 | White et al. |
| 5,121,757 A | 6/1992 | White et al. |
| 5,131,414 A | 7/1992 | Fagg et al. |
| 5,131,415 A | 7/1992 | Munoz et al. |
| 5,148,819 A | 9/1992 | Fagg |
| 5,197,494 A | 3/1993 | Kramer |
| 5,230,354 A | 7/1993 | Smith et al. |

(Continued)

FOREIGN PATENT DOCUMENTS

| | | |
|---|---|---|
| JP | H08165298 | 6/1996 |
| WO | WO 96/31255 | 10/1996 |

(Continued)

OTHER PUBLICATIONS

Curious Cook. "The New York Times" Sep. 15, 2010 [Retrieved from the Internet on: Sep. 28, 2019]. Retrieved from <URL: https://www.curiouscook.com/site/2010/09/achieving-a-distinct-flavor-without-going-to-extremes.html> (Year: 2010)

(Continued)

*Primary Examiner* — Russell G Fiebig
(74) *Attorney, Agent, or Firm* — Womble Bond Dickinson (US) LLP

(57) ABSTRACT

The disclosure describes methods for the purification of protein-enriched extracts to provide concentrates and isolates and methods for incorporation of such materials into products. The purification methods are adapted for removal of nicotine and may have other benefits, e.g., lightening the color of the protein-enriched extracts. The methods generally include treatment with peracetic acid or hydrogen peroxide and filtrations. A protein composition in the form of a concentrate or isolate is provided, the protein composition including RuBisCO, F2 fraction proteins, or combination thereof extracted from a plant of the *Nicotiana* species, wherein the protein composition is characterized by relatively low nicotine content.

7 Claims, 4 Drawing Sheets

(56) References Cited

U.S. PATENT DOCUMENTS

| | | |
|---|---|---|
| 5,234,008 A | 8/1993 | Fagg |
| 5,243,999 A | 9/1993 | Smith |
| 5,301,694 A | 4/1994 | Raymond et al. |
| 5,318,050 A | 6/1994 | Gonzalez-Parra et al. |
| 5,343,879 A | 9/1994 | Teague |
| 5,360,022 A | 11/1994 | Newton et al. |
| 5,435,325 A | 7/1995 | Clapp et al. |
| 5,445,169 A | 8/1995 | Brinkley et al. |
| 5,713,376 A | 2/1998 | Berger |
| 5,900,376 A | 5/1999 | Das et al. |
| 6,033,895 A | 3/2000 | Garger et al. |
| 6,131,584 A | 10/2000 | Lauterbach |
| 6,284,875 B1 | 9/2001 | Turpen et al. |
| 6,298,859 B1 | 10/2001 | Kierulff et al. |
| 6,772,767 B2 | 8/2004 | Mua et al. |
| 6,817,970 B2 | 11/2004 | Berit et al. |
| 6,906,172 B2 | 6/2005 | Bratcher et al. |
| 7,034,128 B2 | 4/2006 | Turpen et al. |
| 7,048,211 B2 | 5/2006 | Bratcher et al. |
| 7,337,782 B2 | 3/2008 | Thompson |
| 9,175,052 B2 | 11/2015 | Gerardi et al. |
| 9,220,295 B2 | 12/2015 | Morton et al. |
| 9,301,544 B2 | 4/2016 | Mua et al. |
| 2010/0093054 A1 | 4/2010 | Lo et al. |
| 2011/0257369 A1 | 10/2011 | Lo et al. |
| 2013/0072661 A1 | 3/2013 | Maningat et al. |
| 2014/0271952 A1* | 9/2014 | Mua ................ A24B 15/24 426/655 |
| 2014/0343254 A1* | 11/2014 | Gerardi ............ A24B 15/24 530/370 |
| 2016/0029663 A1 | 2/2016 | Gerardi et al. |

FOREIGN PATENT DOCUMENTS

| | | |
|---|---|---|
| WO | WO 99/52537 | 10/1999 |
| WO | WO 2005/048929 | 6/2005 |
| WO | WO 2008/143914 | 11/2008 |
| WO | WO 2010/102284 | 9/2010 |
| WO | WO 2011/078671 | 6/2011 |
| WO | WO 2014/159617 | 10/2014 |
| WO | WO 2014/186671 | 11/2014 |

OTHER PUBLICATIONS

Fu et al., "Recovery of Nicotine-Free Proteins From Tobacco Leaves Using Phosphate Buffer System Under Controlled Conditions," *Bioresource Technology*, 2010, vol. 101, pp. 2034-2042.

Hauck et al., "The Manufacture of Allergenic Extracts in North America," *Clinical Review in Allergy and Immunology*, 2001, pp. 93-110, vol. 21.

* cited by examiner

PURIFICATION OF TOBACCO-DERIVED PROTEIN COMPOSITIONS

CROSS-REFERENCE TO RELATED APPLICATIONS

The present application is a divisional of U.S. patent application Ser. No. 15/654,834, filed Jul. 20, 2017, which is incorporated by reference herein in its entirety.

FIELD OF THE INVENTION

The present invention relates primarily to products made or derived from tobacco, or that otherwise incorporate tobacco or components of tobacco, and are intended for human consumption. Of particular interest are ingredients or components obtained or derived from plants or portions of plants from the *Nicotiana* species.

BACKGROUND OF THE INVENTION

Many uses of tobacco have been proposed. For example, tobacco has been smoked in pipes, and tobacco has been used for smoking in cigarettes and cigars. See, for example, *Tobacco Production, Chemistry and Technology*, Davis et al. (Eds.) p. 346 (1999). In recent years, there have been proposed various ways of providing many of the sensations of smoking, but without delivering considerable quantities of incomplete combustion and pyrolysis products that result from burning tobacco. See, for example, the background art set forth in U.S. Pat. No. 7,503,330 to Borschke et al. and U.S. Pat. No. 7,726,320 to Robinson et al., and U.S. patent application Ser. No. 13/840,264 to Novak, III et al., filed Mar. 15, 2013 and U.S. Ser. No. 13/647,670 to Gerardi, filed Oct. 9, 2012. Tobacco also has been enjoyed in so-called smokeless forms. See, for example, the background art set forth in US Pat. Pub. 2012/0272976 to Byrd et al. In addition, various materials derived from tobacco have been proposed to have uses in certain industrial applications. See, for example, U.S. Pat. No. 2,098,836 to Ressler; U.S. Pat. No. 2,232,662 to Hockenyos; U.S. Pat. No. 4,347,324 to Wildman et al. and U.S. Pat. No. 4,289,147 to Wildman et al., and US Pat. Pub. Nos. 2011/01287681 to DeVall and 2012/0260929 to Coleman et al.

Methods of extracting proteins from tobacco and tobacco components have been proposed in U.S. Pat. No. 9,301,544 to Mua et al., which is incorporated herein by reference. Certain methods for purifying such proteins and for compositions incorporating such proteins have been described in U.S. Pat. No. 9,175,052 to Gerardi et al. and US Pat. App. Publ. No. 2016/0029663 to Gerardi et al., respectively. It would be desirable to provide further methods for purifying tobacco-derived proteins, e.g., for inclusion in tobacco formulations useful in the manufacture of smoking articles and/or smokeless tobacco products, as well as for incorporation into other products such as nutritional supplements.

SUMMARY OF THE INVENTION

The present invention provides materials derived from plants, particularly from plants of the *Nicotiana* species. In preferred embodiments, the materials are provided in what can be considered to be substantially purified form. The invention also provides methods for purifying components from plants, e.g., plants of the *Nicotiana* species, and methods for further processing those components. In particular, the invention provides protein concentrates, isolates, and other forms of protein-containing products derived from tobacco material (and particularly, such concentrates, isolates, and other forms with reduced nicotine content). The invention further provides methods for obtaining such protein concentrates, isolates, and other forms of protein-containing products, and methods for incorporation of such protein concentrates, isolates, and other forms of protein-containing products into various types of compositions.

In one aspect, the present disclosure provides a method for reducing the nicotine content in a plant-derived protein-enriched material, the method comprising: a) receiving a plant-derived, protein-enriched material comprising RuBisCO, F2 fraction proteins, or a combination thereof, wherein the plant-derived, protein-enriched material further comprises undesirable nicotine; b) treating the plant-derived, protein-enriched material with peracetic acid to give a peracetic acid-treated mixture; c) washing the peracetic acid-treated mixture with water on a filter, wherein a solid treated protein-containing material is retained on the filter; d) solubilizing the solid treated protein-containing material to give a solution and adjusting the pH of the solution to a basic pH to give a basic solution; and e) processing the basic solution on a filter to afford a retentate comprising a protein concentrate or isolate having a reduced amount of nicotine as compared with the plant-derived, protein-enriched material. In some embodiments, the plant-derived, protein-enriched material comprises material from a plant of the *Nicotiana* species.

Various parameters can be adjusted with respect to each step of this method. In the context of the foregoing method, in some embodiments, treating step b) is conducted at a pH of about 3 to about 5. In some embodiments, the treating step b) is conducted at a temperature of about 25° C. to about 42° C. Treating step b), in certain embodiments, comprises treating the plant-derived, protein-enriched material with peracetic acid in the form of an aqueous solution comprising at least about 3% by weight peracetic acid. Washing step c) can, in some embodiments, comprise washing the peracetic acid-treated mixture with water on a 1.4 µm pore filter. Washing step c) is advantageously done using acidic water, e.g., water having a pH of less than about 5. In some embodiments, step d) comprises resolubilizing the solid treated protein-containing material in an aqueous buffer. The aqueous buffer can vary; in particular embodiments, the aqueous buffer comprises sodium bicarbonate and potassium carbonate. In some embodiments, step e) comprises processing the basic solution on a 10 nm filter. The disclosed method may, in certain embodiments, further comprise spray drying the protein concentrate or isolate.

Advantageously, the resulting protein concentrate or isolate typically exhibits decreased nicotine content with respect to the as-received plant-derived, protein-enriched material. For example, the protein concentrate or isolate in certain embodiments exhibits a nicotine content of about 5 ppm or less or about 2 ppm or less by dry weight. In some embodiments, the protein concentrate or isolate exhibits a greater overall concentration by dry weight of protein (RuBisCO, F2 fraction proteins, or a combination thereof) than in the as-received material. For example, in some embodiments, the concentration can be about 80% or greater by dry weight, e.g., about 80% to about 90% by dry weight. Further, the protein concentrate or isolate in some embodiments is characterized as having better sensory characteristics and can, in some embodiments, be substantially odorless, substantially colorless, and/or substantially tasteless.

In another aspect, the disclosure provides a method for reducing the nicotine content in a plant-derived protein-enriched material, the method comprising: a) receiving a plant-derived, protein-enriched material comprising RuBisCO, F2 fraction proteins, or a combination thereof, wherein the plant-derived, protein-enriched material further comprises undesirable nicotine; b) treating the plant-derived, protein-enriched material with a basic solution to give a base-treated mixture; c) mixing the base-treated mixture with hydrogen peroxide to give a hydrogen-peroxide-treated material; and d) processing the basic solution on a filter to afford a retentate comprising a protein concentrate or isolate having a reduced amount of nicotine as compared with the plant-derived, protein-enriched material.

Various parameters can be adjusted with respect to each step of this method. In the context of the foregoing method, in some embodiments, treating step b) comprises treating the plant-derived, protein-enriched material with the basic solution to a pH of about 10 or greater. In some embodiments, the method further comprises heating the base-treated mixture before, during, or both before and during mixing step c). For example, the base-treated mixture can be heated at a temperature of about 30° C. to about 42° C. In certain embodiments, processing step d) comprises processing the basic solution on a filter with a pore size of about 10 nm or a molecular weight cutoff of about 10 kDa. The method can, in some embodiments, further comprise spray drying the protein concentrate or isolate. Advantageously, the resulting protein concentrate or isolate typically exhibits decreased nicotine content with respect to the as-received plant-derived, protein-enriched material. For example, the protein concentrate or isolate in certain embodiments exhibits a nicotine content of about 30 ppm or less by dry weight.

BRIEF DESCRIPTION OF THE DRAWINGS

In order to provide an understanding of embodiments of the invention, reference is made to the appended drawings, which are not necessarily drawn to scale, and in which reference numerals refer to components of exemplary embodiments of the invention. The drawings are exemplary only, and should not be construed as limiting the invention.

DETAILED DESCRIPTION OF THE PREFERRED EMBODIMENTS

Figure 1:
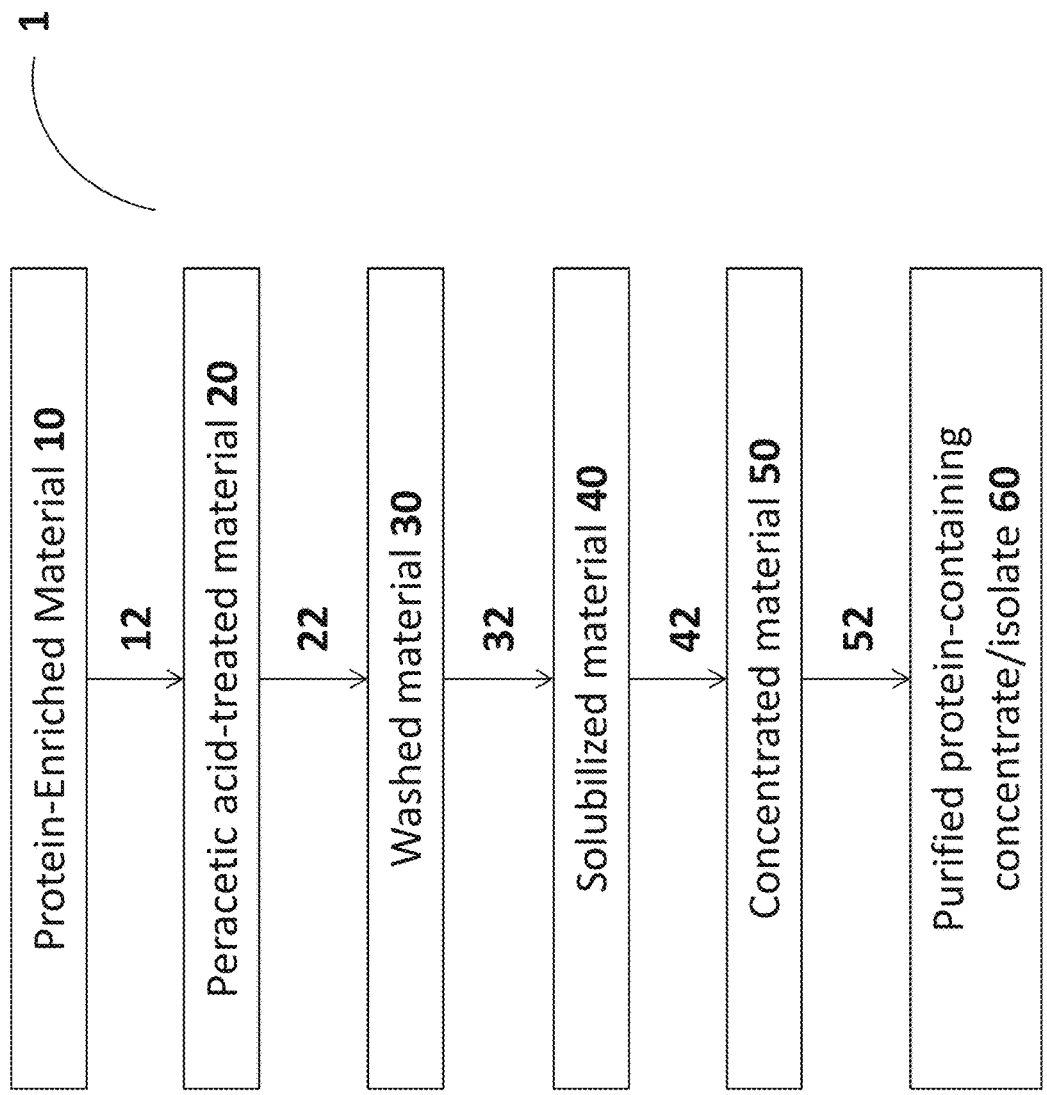
FIG. 1 is a flowchart of method steps associated with one embodiment of the present disclosure.

The present invention now will be described more fully hereinafter. This invention may, however, be embodied in many different forms and should not be construed as limited to the embodiments set forth herein; rather, these embodiments are provided so that this disclosure will be thorough and complete, and will fully convey the scope of the invention to those skilled in the art. As used in this specification and the claims, the singular forms "a," "an," and "the" include plural referents unless the context clearly dictates otherwise. Reference to "dry weight percent" or "dry weight basis" refers to weight on the basis of dry ingredients (i.e., all ingredients except water).

Generally, the present invention provides methods for purifying biomass-derived protein extracts. In one preferred embodiment, the biomass-derived protein extract comprises protein derived from a plant of the *Nicotiana* species. Often, methods of deriving protein from various biomasses results in a protein-enriched material that is not pure protein and may contain various other components extracted from the biomass. For example, in certain embodiments the crude protein-enriched material extracted from the biomass can further comprise such substances as nicotine, lipids, chlorophyll, tannins, minerals, plant structural components, and phenolic pigments.

Although the present disclosure focuses primarily on proteins extracted from tobacco, it is noted that the methods may be generally applicable to crude protein materials extracted from plant materials other than tobacco. The methods described herein are thus intended to be applicable to any plant comprising green leaves and/or any plant believed to comprise proteins. In some embodiments, the methods are applicable to trees, bushes, grasses, ferns, vines, mosses, algae, and herbs. For example, the methods for preparing and purifying a protein-enriched material according to the present disclosure are in some embodiments applicable to such plants as spinach, alfalfa, Swiss chard, kale, chicory, amaranth, barley leaves, mustard greens, clover, carrot leaves, and beet leaves.

According to the present disclosure, a protein-enriched material can be further processed to provide a purer protein composition, such as a composition in the form of a concentrate or isolate. By "protein-enriched material" is meant a material (e.g., an extract) that has been derived from a plant and which contains one or more types of protein. The crude protein-enriched materials described herein generally comprise an amount of undesirable components/impurities such as ash, metal salts, trace metals, alkaloids (e.g., nicotine), precipitates, and other residual materials. Further, the protein-enriched materials may exhibit undesirable sensory or organoleptic characteristics (e.g., taste characteristics, odor, and/or color). By "protein concentrate" as used herein is meant a material comprising between about 29% and about 89% by weight protein on a dry weight basis. By "protein isolate" as used herein is meant a material comprising about 90% or more protein by weight on a dry weight basis.

Advantageously according to the invention, methods are provided for purifying protein-enriched materials to provide concentrates and/or isolates containing minimal amounts of certain undesirable components/impurities. Various methods disclosed herein can provide purified protein isolates comprising about 60% or greater or about 65% or greater by weight protein and low nicotine levels, e.g., about 50 ppm or lower, about 30 ppm or lower, about 20 ppm or lower, about 10 ppm or lower, or about 5 ppm or lower nicotine.

The present disclosure is applicable, in some embodiments, for large scale production, where the term large scale production refers to processing large quantities of a biomass on a mass production level. The term "biomass" and related terms such as "biomatter" and "plant source" are understood to refer to any portion of a harvested plant that may be processed to extract, separate, or isolate components of interest therefrom. The processing may be carried out in relation to various plants or portions thereof, such as seeds, flowers, stalks, stems, roots, tubers, leaves, or any further portions of the plant.

In particular embodiments, the methods described herein can be particularly relevant to the isolation and/or purification of a crude protein-containing material (e.g., extract) obtained from a tobacco plant material or a portion thereof. Exemplary tobacco plant materials used in accordance with the present disclosure may be of some form of a plant of the *Nicotiana* species, as described for example, in U.S. Pat. No. 9,254,001 to Byrd et al., which is incorporated by reference herein. Further descriptions of various types of tobaccos, growing practices and harvesting practices are set forth in *Tobacco Production, Chemistry and Technology*, Davis et al. (Eds.) (1999), which is incorporated herein by reference. Additional information on types of *Nicotiana* species suitable for use in the present invention can be found in U.S. Pat. No. 9,107,453 to Dube et al., which is incorporated by reference herein. The plant material may comprise material derived from an entire plant or any portion of a plant of the *Nicotiana* species. See, for example, the portions of tobacco plants set forth in U.S. Pat. No. 8,955,523 to Coleman, III et al. and U.S. Pat. No. 9,107,453 to Dube et al., which are incorporated by reference herein.

The plant of the *Nicotiana* species can be employed in either an immature or mature form, and can be used in either a green form or a cured form, as described in U.S. Pat. No. 9,107,453 to Dube et al., which is incorporated by reference herein. The tobacco material can be subjected to various treatment processes such as, refrigeration, freezing, drying (e.g., freeze-drying or spray-drying), irradiation, yellowing, heating, cooking (e.g., roasting, frying or boiling), fermentation, bleaching or otherwise subjected to storage or treatment for later use. In some embodiments, harvested tobacco can be sprayed with a buffer or antioxidant (e.g., a sodium metabisulfite buffer) to prevent the green plants from browning prior to further treatment as described herein. Other exemplary processing techniques are described, for example, in U.S. Pat. No. 7,946,295 to Brinkley et al. and U.S. Pat. No. 8,955,523 to Coleman, III et al., which are incorporated by reference herein. At least a portion of the plant of the *Nicotiana* species can be treated with enzymes and/or probiotics before or after harvest, as discussed in US Pat. Appl. Pub. No. 2013/0269719 to Marshall et al. and U.S. Pat. No. 9,485,953 to Moldoveanu, which are incorporated herein by reference.

In particular embodiments, the proteins of the protein-enriched materials to be treated (as well as the proteins comprising the resulting concentrates and isolates described herein) can comprise Fraction 1 ("F1") proteins and/or Fraction 2 ("F2") proteins. F1 proteins and F2 proteins generally make up the water-soluble protein portion of plant biomass. The F1 protein is an enzyme, known as ribulose-1,5-bisphosphate carboxylase-oxygenase (commonly referred to as RuBisCO), whose overall molecular weight is about 550 kD (comprising a large and small subunit with molecular weights of about 55 kDa and about 13 kDa, respectively, with 8 of each subunit forming the F1 protein). RuBisCO is largely considered to be the most abundant protein in the world, as it is present in every plant that undergoes photosynthesis. RuBisCO may comprise up to about 25% of the total protein content of a leaf and up to about 10% of the solid matter of a leaf. RuBisCO is essential to the initial step of the photosynthetic fixation of carbon dioxide and functions to catalyze the carboxylation and/or oxygenation of ribulose-1,5-bisphosphate. The F2 protein is a mixture of soluble proteins of cytoplasmic and chloroplastic origin. The proteins and peptides of the F2 protein generally have molecular weights ranging from about 3 kD to about 100 kD.

In certain embodiments, the protein concentrates treated according to the methods described herein are prepared according to the methods described in U.S. Pat. No. 9,301,544 to Mua et al., which is incorporated herein by reference, the subject matter of which is outlined briefly herein. According to the disclosure of the '544 patent, one exemplary set of processing steps that can be carried out to obtain a RuBisCO-enriched extract and/or a F2 protein-enriched extract from a tobacco plant or portion thereof can include the following steps. A tobacco material is homogenized to provide a solid pulp and a liquid, protein-containing extract. The extract is clarified to remove solids therefrom, giving a solids fraction and a clarified, protein-containing extract. The extract is then pH-adjusted and separated into a liquid component and a solid, protein-containing precipitate. The precipitate generally comprises RuBisCO as well as various additional components. It is noted that the content of the precipitate may depend, in part, on the pH used in the previous step. For example, where the pH is between about 4.5 and about 6, the precipitate may comprise more RuBisCO, whereas where the pH is less than about 4.5, the precipitate may additionally include a significant amount of F2 proteins. The precipitate is subjected to filtration to give a protein-enriched material. Where a significant amount of F2 fraction is contained in the liquid component, that liquid component can be treated, for example, by filtration (e.g., through a filter or membrane on which the F2 proteins are generally retained, while allowing certain remaining components to pass through) or by precipitation (e.g., by adjusting the pH of the liquid component to a pH sufficient to precipitate the F2 proteins, such as less than about 4.5, preferably between about 3 and about 4.5).

An alternative exemplary process disclosed in the '544 patent for the production of a RuBisCO- and F2 protein-enriched material, RuBisCO-enriched material, and/or F2 protein-enriched material comprises the following steps. A tobacco material can be homogenized to provide a solid pulp and a liquid, protein-containing extract. The extract can then be clarified to remove solids therefrom (e.g., via a pH-adjustment step to provide an acidic or basic clarified, protein-containing extract), giving a solids fraction and a clarified, protein-containing extract. The extract is filtered and washed to give a solid, RuBisCO-enriched material, and a permeate. In certain embodiments, the permeate may comprise F2 proteins and the permeate can optionally be processed (e.g., including via filtration methods) to give an F2 protein-enriched material.

In one specific embodiment, protein-enriched material 10 is obtained according to the methods outlined in U.S. Pat. No. 9,301,544, as referenced herein above, which is incorporated by reference in its entirety. However, the disclosure is not understood to be limited to protein-enriched material 10 obtained in this manner. Other exemplary techniques for extracting components of tobacco are described in U.S. Pat. No. 4,144,895 to Fiore; U.S. Pat. No. 4,150,677 to Osborne, Jr. et al.; U.S. Pat. No. 4,267,847 to Reid; U.S. Pat. No. 4,289,147 to Wildman et al.; U.S. Pat. No. 4,351,346 to Brummer et al.; U.S. Pat. No. 4,359,059 to Brummer et al.; U.S. Pat. No. 4,506,682 to Muller; U.S. Pat. No. 4,589,428 to Keritsis; U.S. Pat. No. 4,605,016 to Soga et al.; U.S. Pat. No. 4,716,911 to Poulose et al.; U.S. Pat. No. 4,727,889 to Niven, Jr. et al.; U.S. Pat. No. 4,887,618 to Bernasek et al.; U.S. Pat. No. 4,941,484 to Clapp et al.; U.S. Pat. No. 4,967,771 to Fagg et al.; U.S. Pat. No. 4,986,286 to Roberts et al.; U.S. Pat. No. 5,005,593 to Fagg et al.; U.S. Pat. No. 5,018,540 to Grubbs et al.; U.S. Pat. No. 5,060,669 to White et al.; U.S. Pat. No. 5,065,775 to Fagg; U.S. Pat. No.

5,074,319 to White et al.; U.S. Pat. No. 5,099,862 to White et al.; U.S. Pat. No. 5,121,757 to White et al.; U.S. Pat. No. 5,131,414 to Fagg; U.S. Pat. No. 5,131,415 to Munoz et al.; U.S. Pat. No. 5,148,819 to Fagg; U.S. Pat. No. 5,197,494 to Kramer; U.S. Pat. No. 5,230,354 to Smith et al.; U.S. Pat. No. 5,234,008 to Fagg; U.S. Pat. No. 5,243,999 to Smith; U.S. Pat. No. 5,301,694 to Raymond et al.; U.S. Pat. No. 5,318,050 to Gonzalez-Parra et al.; U.S. Pat. No. 5,343,879 to Teague; U.S. Pat. No. 5,360,022 to Newton; U.S. Pat. No. 5,435,325 to Clapp et al.; U.S. Pat. No. 5,445,169 to Brinkley et al.; U.S. Pat. No. 6,131,584 to Lauterbach; U.S. Pat. No. 6,284,875 to Turpen et al.; U.S. Pat. No. 6,298,859 to Kierulff et al.; U.S. Pat. No. 6,772,767 to Mua et al.; U.S. Pat. No. 6,817,970 to Berit et al.; U.S. Pat. No. 6,906,172 to Bratcher et al.; U.S. Pat. No. 7,034,128 to Turpen et al.; U.S. Pat. No. 7,048,211 to Bratcher et al.; and U.S. Pat. No. 7,337,782 to Thompson, all of which are incorporated by reference herein. See also, the ultrafiltered translucent tobacco extracts set forth in US Pat. Appl. Pub. Nos. 2013/0074855 and 2013/0074856, both to Holton, Jr., which are incorporated by reference herein.

Of course, it is to be understood that various additional processes can be used within these exemplary methods or in addition to the steps of the methods in the references cited herein and the methods described above. For example, typical separation processes can include one or more process steps such as solvent extraction (e.g., using polar solvents, organic solvents, or supercritical fluids), chromatography (e.g., preparative liquid chromatography), clarification, distillation, filtration (e.g., ultrafiltration), recrystallization, and/or solvent-solvent partitioning. In some embodiments, it may be advantageous to conduct solvent extraction using a cold extracting liquid (e.g., water), particularly prior to a subsequent filtration step. Extractions are commonly conducted at elevated temperature; however, subjecting extracts resulting from such extractions directly to filtration may damage the filters, due to the heat associated with the extracts and, as such, hot/warm extracts are typically cooled prior to subsequent filtration steps. This cooling step can be avoided in some embodiments by conducting extractions at room temperature, in which case the resulting extracts can be advantageously directly treated by filtration. In some embodiments, the tobacco plant or portion thereof can be pre-treated, e.g., to liberate certain compounds to make the desired compounds available for more efficient separation. In some embodiments, multiple methods are used to obtain the desired compounds.

Other exemplary means for extraction of proteins from tobacco and other plants include, but are not limited to, those described in U.S. Pat. No. 7,337,782 to Thompson; U.S. Pat. No. 6,033,895 to Garger et al.; U.S. Pat. No. 4,941,484 to Clapp et al.; U.S. Pat. Nos. 4,588,691 and 4,400,471 to Johal; U.S. Pat. No. 4,347,324 to Kwanyuen et al., U.S. Pat. No. 4,340,676 to Bourque; U.S. Pat. No. 4,333,871 to DeJong; U.S. Pat. Nos. 4,289,147 and 4,268,632 to Wildman et al.; U.S. Pat. Nos. 3,959,246, 3,823,128, and 3,684,520 to Bickoff et al.; US Pat. Appl. Publ. Nos. 2010/0093054 to Lo et al. and 2013/0072661 to Kale; US Pat. Appl. No. Int'l Appl. Publ. Nos. WO2011/078671 to Van de Velde et al. and WO2008/143914 to Lo; and EP Pat. Publ. Nos. EP 2403888 to Parker et al.; EP 1691759 to Boddupalli et al.; and EP 1067946 to Brinkhaus et al., which are all incorporated by reference herein in their entireties. Other exemplary processing methods are provided, for example, in U.S. Pat. No. 9,220,295 to Morton et al., which is incorporated herein by reference.

A protein-enriched material 10 used as a starting point in the purification processes discussed herein can be provided in varying forms. In some embodiments, the protein-enriched material is provided in a moistened form. In some embodiments, the protein-enriched extract is subjected to a solvent removal process such that the extract achieves a predominantly solid form. The protein-enriched extracts may be provided in a low solvent form. By the term "low solvent form" is meant that the solvent content including the moisture content of the material (e.g., a protein-enriched tobacco extract) is less than about 12 percent, based on the total weight of the material. Convenient methods for providing the protein-enriched extract in low solvent form include spray drying, freeze drying, belt drying, flash drying, or other such methods. It is particularly desirable to concentrate the liquid extract prior to spray drying or freeze drying the extract. A representative spray drying process is described in U.S. Pat. No. 3,398,754 to Tughan, which is incorporated herein by reference. A representative freeze drying process is described in U.S. Pat. No. 3,316,919 to Green, which is incorporated herein by reference. Methods and conditions for providing extracted materials in a low solvent or solid form (e.g., as a powder) will be apparent to the skilled artisan.

The protein-enriched material 10 typically comprises some percentage of undesirable components and/or features. For example, in some embodiments, the protein-enriched material comprises an undesirable level of nicotine. According to the present disclosure, a protein-containing material (which may, in some embodiments, comprise RuBisCO and/or F2 proteins) isolated from a plant material (e.g., according to various methods as outlined above) is further treated to provide a protein composition (e.g., in the form of a concentrate or isolate) having a lower concentration of one or more of these undesirable components than prior to treatment.

Generally, the methods disclosed herein involve treatment of a protein-enriched material with peracetic acid and/or with hydrogen peroxide, as will be described in further detail herein. Treatment of tobacco and tobacco-derived materials with a range of reagents for various purposes is known. For example, references describing treatment of tobacco with oxidizing agents such as ozone or hydrogen peroxide include, e.g., U.S. Pat. Nos. 3,612,065 and 3,943,945 to Rosen; U.S. Pat. No. 4,641,667 to Schmekel et al.; U.S. Pat. Nos. 4,366,823, 4,366,824, and 4,388,933 to Rainier et al.; U.S. Pat. No. 5,713,376 to Berger; and Int. Appl. Pub. No. WO1996/31255 to Giolvas, which are all incorporated herein by reference.

In certain embodiments, the treatment process is that illustrated in FIG. 1 (Process 1). Generally, the treatment process of FIG. 1 involves a solid material comprising protein (10), typically prepared by extracting a tobacco material to give an aqueous extract and concentrating the extract (as described in detail herein above). Material 10 is subjected to the following steps: 12 (treating material 10 with peracetic acid, giving peracetic acid-treated material 20), 22 (washing peracetic acid-treated material 20 with water on a relatively large, e.g., micron-sized (e.g., 1.4 µm) filter to give washed material 30), 32 (solubilizing washed material 30 and pH adjusting to a basic pH, e.g., about 10 or greater, to give solubilized material 40), 42 (concentrating the solubilized material to give concentrated material 50), and 52 (washing concentrated material 50 on a relatively small, e.g., nanometer-sized (e.g., 10 nm) filter to give purified protein-containing concentrate/isolate 60).

Step 12 involves treating the protein-containing material 10 with peracetic acid to give peracetic acid-treated material 20. Optionally, prior to the addition of peracetic acid, material 10 is first pretreated to a pH of about 3-6, e.g., around 5, which can be achieved using various acids, e.g., including, but not limited to, acetic acid.

Commercially available peracetic acid is generally provided as an aqueous solution and typically contains some concentration of peroxide ($H_2O_2$). Thus, step 12 typically comprises treating material 10 with peracetic acid and peroxide in aqueous solution. The amount of peracetic acid employed in this step can vary, but in some embodiments is an amount of about 0.75% to about 5% peracetic acid by weight or about 1% to about 3% peracetic acid by weight, e.g., about 1% peracetic acid by weight (and about 1% to about 10% peroxide or about 3% to about 8% peroxide, e.g., about 3.5% peroxide by weight), based on the mixture of material 10, peracetic acid, peroxide, and water provided by the peracetic acid/peroxide solution. The contacting can be done at varying temperatures, but in some embodiments, it may enhance the treatment to employ heating during at least a portion of step 12. For example, in certain embodiments, the mixing of protein-enriched material 10, peracetic acid and peroxide can be done at a temperature greater than room temperature, e.g., about 30° C. or greater, or about 35° C. or greater, such as about 25° C. to about 42° C. or about 30° C. to about 42° C. The heating temperature is generally maintained at or below about 42° C. to avoid denaturing the protein. The amount of time for which the protein-containing material 10 is maintained in contact with the peracetic acid/peroxide solution can vary, but is generally at least about 1 hour, at least about 2 hours, or at least about 3 hours (e.g., about 1 to about 5 hours or about 2 to about 5 hours).

The resulting peracetic acid-treated material 20 is typically in the form of a suspension, as the protein present therein is typically precipitated at low pH. Peracetic acid-treated material 20 is next subjected to a washing step 22. Material 20 is typically placed on a relatively large pore size filter sufficient to retain the protein (RuBisCO and/or F2 protein) on the surface of the filter. For example, material 20 can be put on a micron-sized pore filter, such as a 1.4 μm filter (e.g., a 1.4 μm ceramic filter). In some embodiments, tangential flow filtration is used. The washing step 22 involves contacting material 20 with purified water on the filter, allowing the water to remove undesirable components, and retaining the protein on the surface of the filter. The water employed in the washing step advantageously has a pH of less than 7 (i.e., somewhat acidic) to ensure that the protein does not solubilize/stays in a precipitated state, and does not pass through the filter (resulting in loss of desired material). For example, the water advantageously has a pH of about 5 or less or about 4 or less (e.g., purified water with a pH of about 3.5). The water used in washing step 22 is understood, e.g., to quench the peracetic acid remaining from acid treatment step 12 and remove residual peracetic acid (along with possibly other components) from the peracetic acid-treated material 20, which remains on the surface of the filter. The amount of water used to wash material 20 can vary; however, a significant amount of water is generally employed to ensure removal of at least a majority of the peracetic acid from the sample. Similarly, the number of washings conducted can vary, but, again, a sufficient number of washings to ensure removal of at least a majority of the peracetic acid from the sample is preferred. Although not limited thereto, the washing is advantageously conducted based on 2 to 10 times the volume of retentate and, as such, the amount of water employed in the washing (amount per washing and number of washings) may depend upon the volume of material being washed. Washing step 22 is typically conducted at room temperature, although this step is not limited thereto.

The resulting washed material 30 is then solubilized in step 32. The liquid(s) used to solubilize material 30 is advantageously basic (as the proteins are understood to precipitate at low pH and solubility is enhanced as pH is increased). Consequently, step 32 typically involves contacting material 30 with water and base. The specific base can vary, so long as it is capable of providing the desired pH and solubilizing the protein-containing material 30. In some embodiments, a solution of sodium hydroxide (NaOH) is used to achieve the desired pH. The pH of the solution in which material 30 is solubilized during this step is typically about 8 or greater or about 10 or greater, e.g., about 8 to about 16 or about 8 to about 12 (e.g., about 10.5). In some embodiments, the liquid used to solubilize material 30 further comprises a buffer. For example, in one embodiment, a buffer comprising sodium bicarbonate and potassium carbonate is used (which may include various other components that do not negatively interfere with the resolubilization of the protein, e.g., including, but not limited to, sodium metabisulfite). Inclusion of a buffer can, in some embodiments, aid in ensuring the material 30 goes into solution; however, it adds salt content and thus may require a greater extent of washing at a later step to ensure removal of the salts.

The resulting solubilized protein-containing material, in the form of solubilized material 40, is then concentrated (step 42) to give a concentrated material 50. Concentration can be done using methods known in the art for the removal of at least a majority of the liquid associated with solution 40. In preferred embodiments, tangential flow filtration can be used to concentrate the material. Using tangential flow filtration, the material 40 is put on a nanometer-sized pore filter, such as a 10 nm filter (e.g., a 10 nm ceramic filter). Advantageously, the pore size of the filter in step 42 is relatively low; however, the pore size should not be significantly lower than 10 nm, as such pore sizes will likely lead to retention of salts and other undesired components on the surface of the filter. The retentate from this process then comprises concentrated material 50. In some embodiments, concentration can be done by evaporation at room temperature and atmospheric pressure and/or can employ elevated heat (up to about 45° C. or up to about 42° C. to avoid denaturing the protein) and/or applying vacuum). Typically, the material is concentrated so that the material is in substantially solid form, although some liquid may still be associated with concentrated material 50.

The resulting material 50 is then washed 52 in a similar manner as in step 22. However, step 52 generally is conducted on a relatively small pore size filter. For example, material 40 can be put on a nanometer-sized pore filter, such as a 10 nm filter (e.g., a 10 nm ceramic filter). Advantageously, the pore size of the filter in step 52 is relatively low; however, the pore size should not be significantly lower than 10 nm, as such pore sizes will likely lead to retention of salts and other undesired components on the surface of the filter. In some embodiments, tangential flow filtration is used. The washing step 52 involves contacting material 50 with purified water on the filter, allowing the water to remove undesirable components, and retaining the protein on the surface of the filter. The water employed in this washing step may, in some embodiments, be purified water (e.g., having a neutral pH of ~7). The protein is already in precipitated form at this stage of the process and the small pore size of the filter on which the material is washed typically prevents significant passage of desired protein through the filter.

The water used in washing step 52 is understood, e.g., to remove residual base and salts (along with possibly other components) from the protein-containing material 50, which remains on the surface of the filter. The amount of water used to wash the protein-containing material can vary; however, a significant amount of water is generally employed to ensure removal of at least a majority of the base and salts from the sample. Similarly, the number of washings conducted can vary, but again a sufficient number of washings to ensure removal of at least a majority of the base and salts from the sample is preferred. Although not limited thereto, the washing is advantageously conducted based on 2 to 10 times the volume of retentate and, as such, the amount of water employed in the washing (amount per washing and number of washings) may depend upon the volume of material being washed. Washing step 52 is typically conducted at room temperature, although this step is not limited thereto. In certain embodiments, steps 42 and 52 are combined, such that concentration and washing are conducted substantially together. For example, in certain embodiments, tangential flow filtration is employed, which can serve multiple functions, e.g., washing and concentrating the protein-containing material.

Advantageously, material 60 (purified protein-containing concentrate/isolate) is provided in dried or substantially dried form following the washing treatment. The drying can be conducted by concentration/evaporation and/or spray drying by methods known in the art.

Purified protein-containing material 60 generally contains a lower concentration of nicotine than that of a comparable material that has not been subjected to a process comprising steps 12, 22, 32, 42, and 52 as outlined herein above. In some embodiments, the treated material (purified protein-containing concentrate/isolate 60) comprises a lower nicotine content, e.g., less than about 10 ppm or less than about 5 ppm nicotine than protein-enriched material 10. In some embodiments, the treated material 60 exhibits a lighter color (e.g., a light cream/tan color which is lighter in color than the material 10 subjected to treatment). In some embodiments, treated material (purified protein-containing concentrate/isolate 60) has decreased ash and/or decreased fiber with respect to the protein-containing material prior to treatment (i.e., protein-enriched material 10). For example, in some embodiments, protein-containing material 10 is at least about 40% protein, e.g., about 40% to about 60% pure protein by dry weight and the corresponding purified protein-containing concentrate/isolate 60 is at least about 50%, at least about 60%, or at least about 65% pure protein by dry weight. As such, Process 1 as described herein above can, in some embodiments, lead to an increase in purity of a protein-containing material of about 10% or more or about 20% or more.

Figure 2:
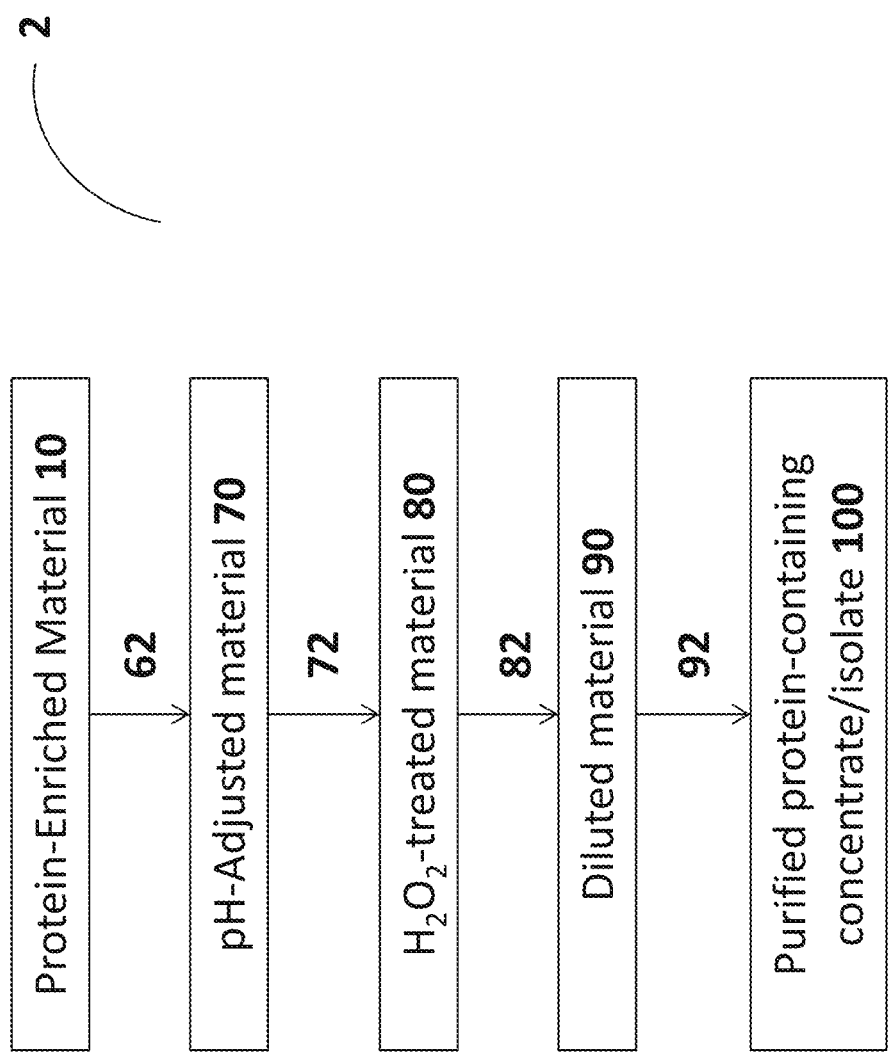
FIG. 2 is a flowchart of method steps associated with another embodiment of the present disclosure.

In another embodiment, the treatment process is that illustrated in FIG. 2 (Process 2). Generally, the treatment process of FIG. 2 involves a solid protein-enriched material (10), typically prepared by extracting a tobacco material to give an aqueous extract and concentrating the extract (as described in detail herein above). Material 10 is subjected to the following steps: 62 (adjusting the pH thereof to a basic pH, giving pH-adjusted material 70), 72 (treating the pH-adjusted material with hydrogen peroxide ($H_2O_2$), giving $H_2O_2$-treated material 80), 82 (diluting the $H_2O_2$-treated material to give diluted material 90), and 92 (washing the $H_2O_2$-treated material on a relatively small pore size, e.g., nanometer-sized (e.g., 10 nm) filter to give purified protein-containing concentrate/isolate 100).

Step 62 involves treating protein-enriched material 10 with a basic solution to give pH-adjusted material 70. In one particular embodiment, sodium hydroxide or potassium hydroxide is used as the base for this step, although this method step is not limited thereto and any base capable of providing the referenced pH can be used. Typically, the base is provided in aqueous solution and, as such, pH-adjusted material 70 is generally in the form of a solution. The amount of base employed in this step can vary, but is typically that amount needed to achieve a basic pH of the mixture, e.g., about 8 or greater, about 9 or greater, or about 10 or greater (e.g., about 8 to about 11 or about 10 to about 10.5).

Although not required, the resulting pH-adjusted material 70 is then generally heated. The subsequent step (step 72) can be conducted at room temperature; however, step 72 may be more effective in some embodiments if the pH-adjusted material is heated. Step 72 involves contacting (e.g., mixing) the pH-adjusted material with hydrogen peroxide ($H_2O_2$). The optional heating can be done prior to contacting material 70 with the hydrogen peroxide and/or during the contacting. The temperature to which material 70 is optionally heated prior to and/or during the contacting step can vary, but in some embodiments can be a temperature greater than room temperature, e.g., about 30° C. or greater, or about 35° C. or greater, such as about 25° C. to about 45° C. or about 30° C. to about 42° C. The heating temperature is generally maintained at or below about 45° C. or at or below about 42° C. to avoid denaturing the protein.

The amount of time for which the pH-adjusted material 70 is maintained in contact with the $H_2O_2$ can vary, but is generally at least about 1 hour, at least about 2 hours, or at least about 3 hours (e.g., about 1 to about 5 hours or about 2 to about 5 hours). The $H_2O_2$ with which the extract is contacted during step 72 can vary in concentration, but is typically in the form of an aqueous solution. For example, in some embodiments, commercially available $H_2O_2$ solutions (e.g., understood to have various concentrations, depending on the intended application, including solutions with $H_2O_2$ concentration of about 3%, about 6%, or about 34.5% by weight) is used and can be diluted to achieve the desired overall concentration of $H_2O_2$. Typically, although not limited thereto, sufficient $H_2O_2$ (e.g., in the form of an aqueous solution) is used to provide an $H_2O_2$ concentration of at least about 1% by weight (based on $H_2O_2$ and water), about 2% by weight, or at least about 3% by weight (e.g., about 1% by weight to about 5% by weight, e.g., about 2% by weight to about 4% by weight).

The addition of $H_2O_2$ solution to pH-adjusted material 70 may result in vigorous reaction. Typically, although not required, some foaming is observed upon contact between pH-adjusted material 70 and the $H_2O_2$. Accordingly, in certain embodiments, the reaction is monitored and parameters are adjusted, e.g., to ensure the reaction is not overly vigorous. For example, the pH is generally monitored to ensure a pH close to that prior to step 70, i.e., a basic pH. The temperature is also commonly monitored to ensure the temperature remains within the ranges referenced above, particularly if heating is employed (e.g., less than about 45° C. or less than about 42° C., such as about 25° C. to about 42° C. or about 30° C. to about 42° C. The mixture may optionally be stirred during step 72 and such optional stirring is typically done gently, again to ensure the reaction is not too vigorous. The time for which material 70 is kept in contact with the $H_2O_2$ can vary and exemplary, although not limiting time periods for step 72 are about 1 hour or more, about 2 hours or more, or about 3 hours or more (e.g., about 2 to about 6 hours or about 3 to about 4 hours).

The resulting $H_2O_2$-treated material 80 is next diluted 82 with water to give diluted material 90. The dilution of material 80 with water serves multiple purposes. For example, the dilution can quench remaining $H_2O_2$ used in step 72. Dilution also helps to protect equipment (e.g., filters) used in subsequent processing steps. The extent of dilution can vary. In some embodiments, material 80 is diluted 1:1 with water by volume or about 1:2 with water by volume; however, the disclosure is not limited thereto.

The resulting diluted material 90 is then washed 92, typically on a relatively small pore size filter. For example, in some embodiments, material 90 can be washed on a nanometer-sized pore filter, such as a 10 nm filter (e.g., a 10 nm ceramic filter). In some embodiments, material 90 can be washed on a 10 kDa membrane (e.g., spiral-wound membrane) filter. Advantageously, the pore size (or molecular weight cutoff, MWCO) of the filter in washing step 92 is relatively low; however, the pore size (or MWCO) should not be significantly lower than 10 nm (or significantly lower than 10 kDa) as such pore sizes/MWCOs will likely lead to retention of salts and other undesired components on the surface of the filter. In some embodiments, tangential flow filtration is used. The washing step 92 involves contacting material 90 with purified water on the filter, allowing the water to remove undesirable components, and retaining the protein on the surface of the filter. The water employed in this washing step may, in some embodiments, be purified water (e.g., having a neutral pH of ~7). The protein is already in precipitated form at this stage of the process and the small pore size of the filter on which the material is washed typically prevents significant passage of desired protein through the filter. The water used in washing step 92 is understood, e.g., to remove residual base and salts (along with possibly other components) from the protein-containing material which remains on the surface of the filter, giving purified protein-containing concentrate/isolate 100. The amount of water used to wash the protein-containing material can vary; however, a significant amount of water is generally employed to ensure removal of at least a majority of the base and salts from the sample. Similarly, the number of washings conducted can vary, but again a sufficient number of washings to ensure removal of at least a majority of the base and salts from the sample is preferred (e.g., 2 times to about 10 times, e.g., at least 2 times or at least 3 times). Washing step 92 is typically conducted at room temperature, although this step is not limited thereto. Advantageously, purified protein-containing concentrate/isolate 100 is provided in dried or substantially dried form following the washing treatment. The drying can be conducted by concentration/evaporation and/or spray drying by methods known in the art.

Purified protein-containing material 100 generally contains a lower concentration of nicotine than that of a comparable material that has not been subjected to a process comprising steps 62, 72, 82, and 92 as outlined herein above. In some embodiments, the treated material 100 comprises a lower nicotine content, e.g., about 40 ppm or less, about 30 ppm or less, or about 25 ppm or less nicotine. In some embodiments, the treated material 100 exhibits a lighter color (e.g., a light greenish color which is lighter in color than the material 10 subjected to treatment). In some embodiments, treated material 100 has decreased ash and/or decreased fiber with respect to the material 10 prior to treatment. For example, in some embodiments, the protein-containing material 10 is at least about 40% protein, e.g., about 40% to about 60% pure protein by dry weight and the corresponding treated material 100 is at least about 50%, at least about 60%, or at least about 65% pure protein by dry weight. As such, Method 2 as described herein above can, in some embodiments, lead to an increase in purity of a protein-containing material of about 10% or more or about 20% or more.

Advantageously, in certain embodiments, the protein composition provided via Method 1 or Method 2 can thus exhibit a reduced nicotine content as compared with the protein-enriched extract. For example, in certain embodiments, the methods outlined herein can reduce the nicotine content by at least about 20%, at least about 30%, at least about 40%, at least about 50%, at least about 60%, at least about 70%, at least about 80% relative to the protein-enriched extract (prior to treatment via Method 1 or Method 2). For example, in some embodiments, the disclosed methods can reduce the nicotine content by between about 5% and about 100%, e.g., between about 20% and about 100%, or between about 50% and about 100%) relative to the protein-enriched extract (prior to supercritical extraction). As referenced above, these methods can, in some embodiments, provide other benefits, e.g., with respect to taste, flavor, and/or odor. For example, in some embodiments, the protein-enriched extract can exhibit an off-taste (e.g., a salty or otherwise negative taste), which can be significantly reduced or muted by the disclosed methods. Similarly, in some embodiments, the protein-enriched extract can exhibit an off-odor (e.g., an earthy odor), which can be significantly reduced or removed by the disclosed methods. Further, the protein-enriched extract can exhibit a color (e.g., yellowish, brownish) that can be significantly reduced or removed by the disclosed methods. The improvement in odor, taste, and/or color of the treated material over the untreated extract can be quantified by any known method. For example, a sensory panel can be used to evaluate the change in odor and or taste, whereas optical methods (e.g., light absorption) can be used to evaluate the change in color. Accordingly, in certain embodiments, a tasteless, colorless, and/or odorless protein concentrate or isolate is provided according to the methods described herein.

The form of the protein composition provided according to the present invention (e.g., a RuBisCO concentrate or isolate, combined RuBisCO/F2 protein concentrate or isolate, and/or F2 concentrate or isolate) obtained according to the methods of the present disclosure can vary. Typically, these materials are in solid, liquid, or semi-solid or gel forms. The resulting formulations can be used in concrete, absolute, or neat form. Solid forms of the concentrates or isolates described herein can include spray-dried and freeze-dried forms. Liquid forms of the concentrates or isolates described herein can include formulations contained within aqueous or organic solvent carriers.

The methods disclosed herein may, in some embodiments, provide a protein concentrate or isolate comprising at least about 50%, at least about 60%, at least about 70%, at least about 80%, or at least about 90% protein by dry weight. In some embodiments, the protein concentrate or isolate comprises a mixture of RuBisCO and F2 proteins. In some embodiments, the protein in the protein concentrate or isolate comprises primarily RuBisCO (including at least about 90%, at least about 95%, or at least about 99% RuBisCO). In some embodiments, the protein in the protein concentrate or isolate comprises primarily F2 protein (including at least about 90%, at least about 95%, or at least about 99% F2 protein).

In some embodiments, the protein concentrate or isolate comprises at least about 50%, at least about 60%, at least about 70%, at least about 80%, or at least about 90% F1 protein by weight. In some embodiments, the present disclosure specifically provides a method for the isolation and/or purification of RuBisCO extracted from a plant of the Nicotiana species or a portion thereof. Accordingly, the methods disclosed herein may, in some embodiments, provide a RuBisCO concentrate or isolate, e.g., a material comprising at least about 50%, at least about 60%, at least about 70%, at least about 80%, or at least about 90% RuBisCO by dry weight. In some embodiments, the protein concentrate or isolate comprises at least about 50%, at least about 60%, at least about 70%, at least about 80%, or at least about 90% F2 protein by dry weight.

Although in some embodiments, the protein concentrate or isolate described herein can be used directly following the one or more treatment steps, it may be desirable to thermally treat the material in order to, for example, pasteurize the material or otherwise chemically alter the material. See, for example, US Pat. Pub. No. 2010/0300463 to Chen et al., which is incorporated herein by reference. In some embodiments, in addition to or in place of the optional heat treatment, tobacco material can be irradiated (e.g., to ensure no microbes are associated with the protein concentrate or isolate).

In some embodiments, the methods described herein can be used in combination with other types of treatment processes, which may, for example, further purify or modify the concentrate or isolate. For example, in some embodiments, the protein-enriched composition is brought into contact with an imprinted polymer or non-imprinted polymer such as described, for example, in US Pat. Pub. Nos. 2007/0186940 to Bhattacharyya et al; 2011/0041859 to Rees et al.; and 2011/0159160 to Jonsson et al; and U.S. patent application Ser. No. 13/111,330 to Byrd et al., filed May 19, 2011, all of which are incorporated herein by reference. Treatment with a molecularly imprinted or non-imprinted polymer can be used to remove certain components of the protein-enriched composition. In some embodiments, the protein-enriched composition described herein can be subjected to conditions so as to cause compounds contained in such material to undergo chemical transformation and/or degradation. Exemplary chemical transformation techniques are set forth in US Pat. Appl. Pub. Nos. 2011/0174323 to Coleman, III, et al. and 2011/0259353 to Coleman, III et al., which are incorporated by reference herein. In some embodiments, other "cleanup" methods can be conducted before or after the disclosed methods, e.g., removal of one or more of ash, metal salts, alkaloids, particulates, heavy metals, etc. from extracts, as disclosed in U.S. Pat. No. 9,175,052 to Gerardi et al, which is incorporated herein by reference in its entirety.

The protein concentrates and isolates (i.e., RuBisCO concentrates and isolates, combined RuBisCO/F2 protein concentrates and isolates, and/or F2 protein concentrates and isolates) provided following any one or more of the purification treatment processes described herein can advantageously be used in various applications. For many applications (e.g., food products, feed products, and industrial products), it may be desirable to replace certain animal proteins with plant proteins. Additionally, in some applications, it may be desirable to replace certain other plant proteins typically used (e.g., soy proteins and/or genetically modified proteins). Protein concentrates and isolates such as those provided by the methods described herein can exhibit good nutritional properties and, in some embodiments, can be provided in a form that has a reduced content of various undesirable components (e.g., ash, metal salts, alkaloids (e.g., nicotine), heavy metals, and other impurities/contaminants) and/or modified sensory characteristics (e.g., odor, taste, and/or color), making them particularly suitable for use in various products. Further, certain physical properties of RuBisCO render it advantageous for use in such products, as it has excellent binding, gelling, solubility, and emulsifying behavior. In some embodiments, the types of treatment described herein may provide a food-grade protein-containing material. In certain embodiments, the protein concentrate isolate comprises a protein material that exceeds soy protein in nutritional quality. In some embodiments, the protein concentrate or isolate may be useful for medicinal purposes.

Processed materials that are provided in accordance with the present invention are useful ingredients for a wide variety of commercial applications. The materials can be used as binders, fillers or extenders, or can serve other functions or impart functional attributes, in a wide variety of industrial formulations. For example, the materials can be used as components of various types of resins that have industrial applications; and additionally can be used as components of coatings (e.g., for inks and paints) and of adhesives (e.g., for glues and hot melt formulations). The materials can be used as components of a wide variety of cosmetic formulations (e.g., the materials can be incorporated within shampoos and skin care products). The materials can be used as components of foods, dietary supplements and functional foods (e.g., as components of beverages, processed food products, and the like). The materials also can be used components of animal feed. The materials can be used as components of pharmaceutical formulations (e.g., as components of liquids, gums, lozenges, tablets and pills that are used for medicinal purposes). Additionally, the materials can be used as components of tobacco products; such as components of tobacco burning products (e.g., cigarettes, cigars, pipe tobaccos, and the like), tobacco heating smoking articles (e.g., cigarettes such as those sold under the brand name Eclipse by R. J. Reynolds Tobacco Company), smokeless tobacco products (e.g, moist snuff, chewing tobacco, snus and so-called dissolvable tobacco products), so-called electronic cigarettes, and the like.

With regard to use in tobacco burning products, the concentrates and isolates described herein can be used in various capacities. For example, in certain embodiments, the concentrates and isolates can be mixed with casing materials and applied to tobacco as a casing ingredient or as a top dressing, incorporated into a cigarette filter (e.g., in the filter plug, plug wrap, or tipping paper) or incorporated into cigarette wrapping paper, preferably on the inside surface, during the cigarette manufacturing process. See, for example, the description and references related to tobacco isolates used in smoking articles set forth in US Pat. Pub. No. 2012/0192880 to Dube et al., which is incorporated by reference herein. Representative tobacco blends, non-tobacco components, and representative cigarettes manufactured therefrom are also set forth in the Dube et al. reference noted above.

Figure 3:
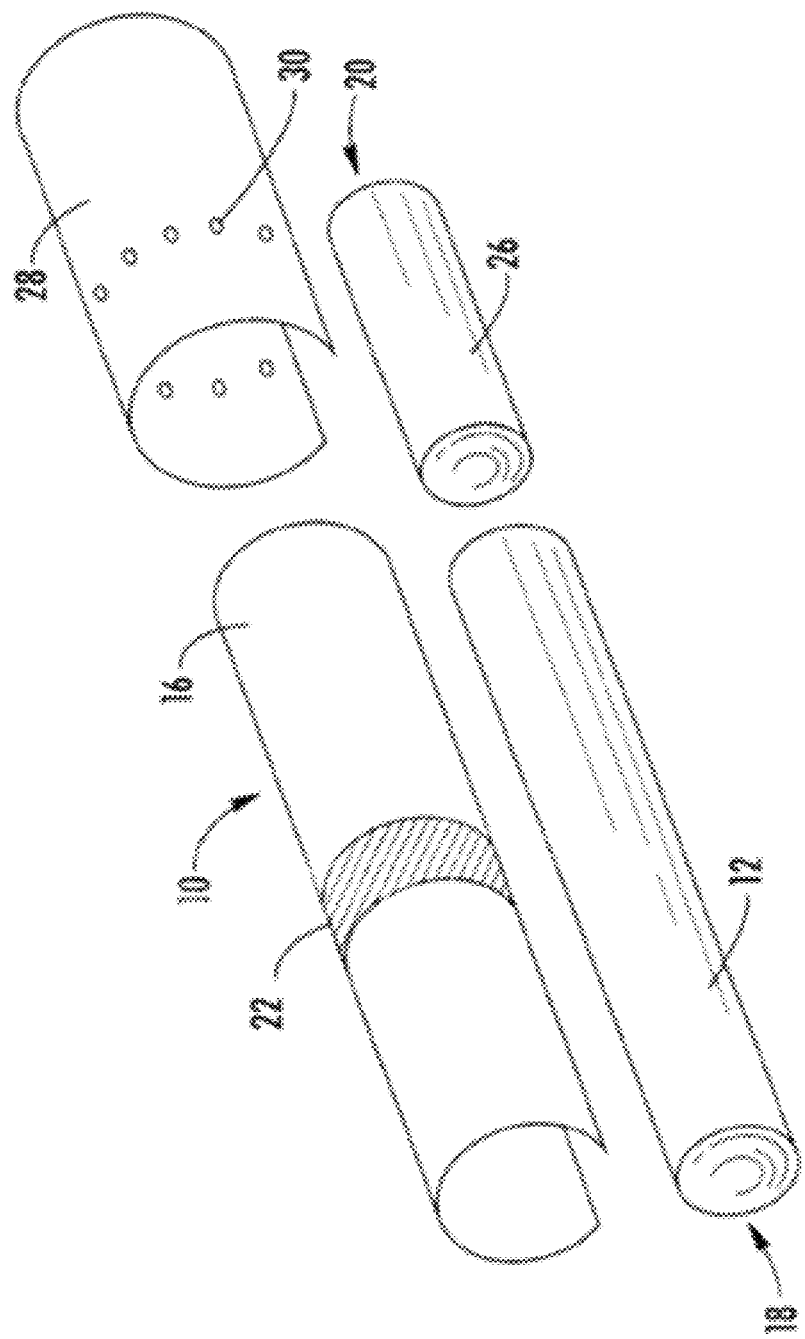
FIG. 3 is an exploded perspective view of a smoking article having the form of a cigarette, showing the smokable material, the wrapping material components, and the filter element of the cigarette.

Referring to FIG. 3, there is shown a smoking article 10 in the form of a cigarette and possessing certain representative components of a smoking article that can contain the protein composition of the present invention. The cigarette 10 includes a generally cylindrical rod 12 of a charge or roll of smokable filler material (e.g., about 0.3 to about 1.0 g of smokable filler material such as tobacco material) contained in a circumscribing wrapping material 16. The rod 12 is conventionally referred to as a "tobacco rod." The ends of the tobacco rod 12 are open to expose the smokable filler material. The cigarette 10 is shown as having an optional band 22 (e.g., a printed coating including a film-forming agent, such as starch, ethylcellulose, or sodium alginate) applied to the wrapping material 16, and that band circumscribes the cigarette rod in a direction transverse to the longitudinal axis of the cigarette. The band 22 can be printed on the inner surface of the wrapping material (i.e., facing the smokable filler material), or less preferably, on the outer surface of the wrapping material.

At one end of the tobacco rod 12 is the lighting end 18, and at the mouth end 20 is positioned a filter element 26. The filter element 26 positioned adjacent one end of the tobacco rod 12 such that the filter element and tobacco rod are axially aligned in an end-to-end relationship, preferably abutting one another. Filter element 26 may have a generally cylindrical shape, and the diameter thereof may be essentially equal to the diameter of the tobacco rod. The ends of the filter element 26 permit the passage of air and smoke therethrough.

A ventilated or air diluted smoking article can be provided with an optional air dilution means, such as a series of perforations 30, each of which extend through the tipping material and plug wrap. The optional perforations 30 can be made by various techniques known to those of ordinary skill in the art, such as laser perforation techniques. Alternatively, so-called off-line air dilution techniques can be used (e.g., through the use of porous paper plug wrap and pre-perforated tipping paper). The protein composition of the invention can be incorporated within any of the components of a smoking article, including but not limited to, as a component of the tobacco charge, as a component of the wrapping paper (e.g., included within the paper or coated on the interior or exterior of the paper), as an adhesive, as a filter element component, and/or within a capsule located in any region of the smoking article.

With regard to use of the disclosed protein compositions in aerosol-generating devices that contain nicotine and/or tobacco material (or some portion or component thereof) that is not intended to be combusted during use, including so-called "e-cigarettes," exemplary details are provided, for example, in US Pat. Pub. No. 2012/0192880 to Dube et al., which is incorporated by reference herein. See, for example, the various alternative smoking articles, aerosol delivery devices and heat generating sources set forth in the background art described in U.S. Pat. No. 7,726,320 to Robinson et al., U.S. patent application Ser. No. 13/432,406, to Griffith, Jr. et al., filed Mar. 28, 2012, U.S. patent application Ser. No. 13/536,438, to Sebastian et al., filed Jun. 28, 2012, U.S. patent application Ser. No. 13/602,871, to Collett et al., filed Sep. 4, 2012, U.S. patent application Ser. No. 13/647,000, to Sears et al., filed Oct. 8, 2012, and U.S. patent application Ser. No. 13/840,264, to Novak, III et al., filed Mar. 15, 2013, which are incorporated herein by reference.

With regard to use of the disclosed concentrates and isolates in smokeless tobacco products, exemplary products include loose moist snuff (e.g., snus); loose dry snuff; chewing tobacco; pelletized tobacco pieces; extruded or formed tobacco strips, pieces, rods, cylinders or sticks; finely divided ground powders; finely divided or milled agglomerates of powdered pieces and components; flake-like pieces; molded tobacco pieces; gums; rolls of tape-like films; readily water-dissolvable or water-dispersible films or strips; meltable compositions; lozenges; pastilles; or capsule-like materials possessing an outer shell and an inner region. Various types of smokeless tobacco products are described or referenced in US Pat. Pub. No 2012/0152265 to Dube et al., which is incorporated herein by reference. Further ingredients can be admixed with, or otherwise incorporated within, smokeless tobacco compositions according to the invention. Exemplary encapsulated additives are described, for example, in WO 2010/132444 to Atchley, which has been previously incorporated by reference herein. See also, the smokeless tobacco ingredients set forth in US Pat. Pub. Nos. 2012/0055494 to Hunt et al. and 2012/0199145 to Byrd et al., which are incorporated by reference herein.

Figure 4:
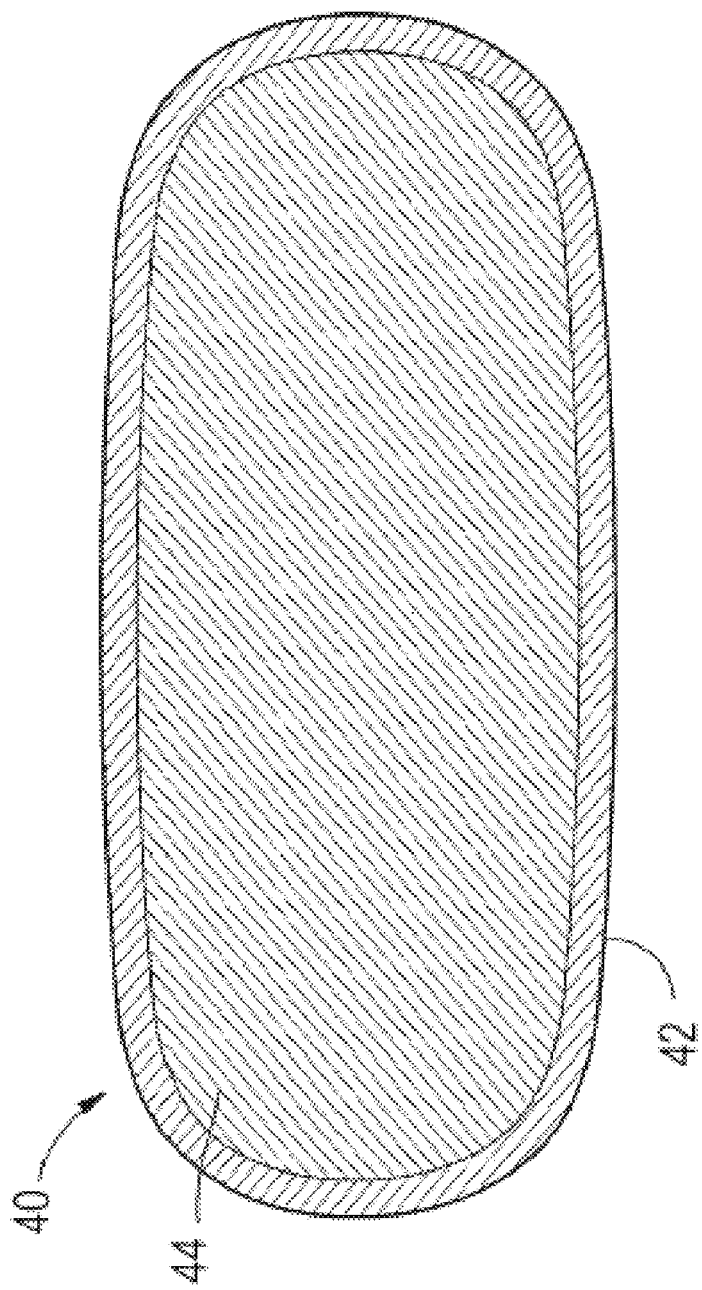
FIG. 4 is a cross-sectional view of a smokeless tobacco product embodiment, taken across the width of the product, showing an outer pouch filled with a smokeless tobacco composition of the invention.

Referring to FIG. 4, a representative snus type of tobacco product comprising a concentrate or isolate of the present invention is shown. In particular, FIG. 4 illustrates a smokeless tobacco product 40 having a water-permeable outer pouch 42 containing a smokeless tobacco composition 44. Any of the components of the tobacco product can comprise a tobacco-derived protein material as described herein (e.g., the interior or exterior of the pouch lining or a portion of the smokeless tobacco composition contained therein).

The amount of protein concentrate or isolate of the present invention incorporated within a tobacco composition or tobacco product can depend on the desired function of the concentrate or isolate, the chemical makeup of the concentrate or isolate, and the type of tobacco composition to which the concentrate or isolate is added. The amount of concentrate or isolate added to a tobacco composition can vary, but will typically not exceed about 50 weight percent based on the total dry weight of the tobacco composition to which the concentrate or isolate is added. For example, the amount of concentrate or isolate added to a tobacco composition may be in the range of about 0.25 to about 25 weight percent or about 1 to about 10 weight percent, based on the total dry weight of the tobacco composition.

Although the use of such protein concentrates and isolates is generally described in the context of tobacco compositions, it is noted that such formulations can be applicable in many other types of compositions, e.g., in dietary supplements as described in U.S. patent application Ser. No. 13/830,063 to Mua et al., filed Mar. 14, 2013, which is incorporated herein by reference.

EXPERIMENTAL

Aspects of the present invention is more fully illustrated by the following examples, which are set forth to illustrate certain aspects of the present invention and are not to be construed as limiting thereof.

Example 1

Exemplary Treatment of RuBisCO-Enriched Extract (Method 1)

Tobacco plants are harvested and the whole plants are chopped in the field. The whole plants are extracted using a 0.75:1 weight to weight ratio of buffer to tissue, using a buffer consisting of 30 mM sodium bicarbonate, 105 mM potassium carbonate and 1% sodium metabisulfite. Fibrous material is separated from green juice, containing the protein. This green juice has a target pH of about 7.5-8.0 (and the pH is not adjusted unless far outside of this range). The green juice is chilled to less than 10° C. and the cooled green juice is passed into a decanter centrifuge at 15 LPM, 30 PSI back pressure. A solid pellet is removed from the liquid and the liquid is then passed to a disk stack at 8 LPM, 75 PSI back pressure. Again, a solid pellet is removed therefrom and the liquid is passed to a filter press, wherein the pH of the liquid is adjusted to 6.5 with dilute HCl. The material is treated with 10 g/L diatomaceous earth and washed 7× volumes with extract buffer with blow down using compressed air. The liquid passing through the filter press is processed on a 0.1 µm ceramic filter, concentrated thereon, and washed with a solution containing 3.0 mM $NaHCO_3$, 10.5 mM $K_2CO_3$, and 0.1% sodium metabisulfite.

The retentate from the ceramic filter is treated with 1% peracetic acid and 3.5% $H_2O_2$. This material is mixed at 40° C.±2° C. for 3 hours at pH about 3.5 or lower. The treated material is processed on a 1.4 µm ceramic filter. The retentate is concentrated and washed 7× with purified water (pH 3.5). This washed retentate is resolubilized by diluting the mixture in a 1:1 weight:weight ratio with a solution containing 3.0 mM $NaHCO_3$, 10.5 mM $K_2CO_3$, and 0.1% sodium metabisulfite and the solution is pH adjusted to 10.5 with NaOH. The resulting mixture is processed on a 10 nm ceramic filter and the retentate is concentrated and washed 7× with purified water (pH ~7). The washed solid is spray dried to provide a purified protein-containing material.

The material thus obtained was determined to have less than 2 ppm nicotine. In particular, the material contained about 70% amino acids by dry weight, with 120 ppm nicotine prior to treatment. After this treatment, it contained about 80% amino acids with <1.68 ppm of nicotine (which was the limit of quantitation by analytical methods). The product also exhibited greatly improved sensory characteristics, i.e., was largely odorless, colorless, and tasteless.

Example 2

Exemplary Treatment of RuBisCO-Enriched Extract (Method 2)

Tobacco plants are harvested, leaves are stripped from the stalks, and the leaves are homogenized in a disintegrator by adding water thereto and the material is then passed into a horizontal screw press for liquid extraction. The liquid protein-containing extract thus obtained is a green juice having a pH of 8.4. This protein-containing extract is clarified first by passing the extract through a decanter.

The filtrate is concentrated on a 0.1 µm ceramic filter and washed 7× with a buffer (containing 3.0 mM $NaHCO_3$, 10.5 mM $K_2CO_3$, and 0.1% sodium metabisulfite). Once washed, the retentate is concentrated and the retentate is pH adjusted to 10.0-10.5 by addition of a 10N NaOH solution. The pH adjusted retentate is heated to 40° C.±2° C. Once at this temperature, the pH of the mixture is checked and readjusted if necessary to ensure a pH of 10.0-10.5. A solution of 34.5% hydrogen peroxide at 100 mL/L is added with very gentle stirring. The mixture is held at 40° C.±2° C. and mixed gently for 3-4 hours. After this time, the mixture is diluted 2× with purified water and processed on a 10 nm ceramic filter. The retentate is concentrated and washed 7× with purified water (pH ~7). The resulting mixture is washed 14× with USP water and the material is reconcentrated to the initial volume. The retentate is spray dried to provide a purified protein-containing material.

The material contained about 70% amino acids by dry weight, with 120 ppm nicotine prior to treatment. After this treatment, it contained a comparable amount of amino acids with about 30 ppm of nicotine. The product also exhibited greatly improved sensory characteristics, i.e., with a significant decrease in odor and taste. The color changed from a dark brown/green to a light green color.

Many modifications and other embodiments of the invention will come to mind to one skilled in the art to which this invention pertains having the benefit of the teachings presented in the foregoing description. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

What is claimed is:

1. A method for reducing the nicotine content in a plant-derived protein-enriched material, the method comprising:
   a) receiving a plant-derived, protein-enriched material comprising RuBisCO, F2 fraction proteins, or a combination thereof, wherein the plant-derived, protein-enriched material further comprises undesirable nicotine;
   b) treating the plant-derived, protein-enriched material with a basic solution to give a base-treated mixture;
   c) mixing the base-treated mixture with hydrogen peroxide to give a hydrogen-peroxide-treated material; and
   d) processing the basic solution on a filter to afford a retentate comprising a protein concentrate or isolate having a reduced amount of nicotine as compared with the plant-derived, protein-enriched material.

2. The method of claim 1, wherein the treating step b) comprises treating the plant-derived, protein-enriched material with the basic solution to a pH of at least about 10.

3. The method of claim 1, further comprising heating the base-treated mixture before, during, or both before and during mixing step c).

4. The method of claim 3, wherein the base-treated mixture is heated at a temperature of about 30° C. to about 42° C.

5. The method of claim 1, wherein the processing step d) comprises processing the basic solution on a filter with a pore size of about 10 nm or a molecular weight cutoff of about 10 kDa.

6. The method of claim 1, further comprising spray drying the protein concentrate or isolate.

7. The method of claim 1, wherein the protein concentrate or isolate comprises about 30 ppm nicotine or less.

* * * * *